US005916570A

United States Patent [19]

Kapil

[11] Patent Number: 5,916,570
[45] Date of Patent: Jun. 29, 1999

[54] MULTIVALENT BOVINE CORONAVIRUS VACCINE AND METHOD OF TREATING BOVINE CORONAVIRUS INFECTION

[75] Inventor: Sanjay Kapil, Manhattan, Kans.

[73] Assignee: Kansas State University Research Foundation, Manhattan, Kans.

[21] Appl. No.: 08/795,294

[22] Filed: Feb. 4, 1997

Related U.S. Application Data

[63] Continuation of application No. 08/489,614, Jun. 12, 1995, abandoned.

[51] Int. Cl.[6] ........................ A61K 39/215; C12N 15/15; C12N 7/04

[52] U.S. Cl. .................................... 424/222.1; 435/173.3; 435/236; 435/237; 435/239; 536/23.1; 536/23.72; 530/826

[58] Field of Search ................................ 424/24.1, 222.1; 435/236, 237, 239, 173.3; 536/23.1, 23.72; 530/826

[56] References Cited

U.S. PATENT DOCUMENTS

| | | | |
|---|---|---|---|
| 3,838,004 | 9/1974 | Mebus et al. | 195/1.3 |
| 3,839,556 | 10/1974 | Mebus et al. | 424/89 |
| 3,869,547 | 3/1975 | Mebus et al. | 424/89 |
| 3,914,408 | 10/1975 | Mebus | 424/89 |

OTHER PUBLICATIONS

Lai Current Topics in Microbiology and Immunology vol. 176 21–32, 1992.
Kapil et al J Vet Diagn Invest vol 7 538–539, 1995.
Kapil et al J Vet Diagn Invest vol 8 96–99, 1996.
Fields et al Fields Virology Third Edition Lippincott–Raven Publishers Chapter 34, 1996.
Bukh et al Seminars in Liver Disease vol. 15 No 1 41–63, 1995.
Wang et al Virology vol. 192 710–716, 1993.
Keck et al Journalof Virology VOl 62 No 5 1810–1813, May 1988.
Browining et al Cell Vol. 72 847–856, Mar. 1993.
Siddell; the Coronaviridae; Plenum Press, New York, 1995; Chapter I. pp. 1–10.
Benedetto et al 1980 Virology 106: 123–132.
Clark, M.A.; 1993, Bovine coronavirus. Br. Vet. J. 149:51–70.
St. Cyr–Coats, K. et al.; 1988, Bovine coronavirus–induced cytopathic expression and plaque formation: Host cell and virus strain determine trypsin dependence; J. Vet. Sci. B. 35:48–56.
Hirano, N. et al.; 1985. Plaque assay of bovine coronavirus in BEK–1 cells. Jpn. J. Vet Sci. 47: 679–681.

Kapil, S. et al.; 1994. Effect of rolling, spinning and sample preparation on isolation of bovine coronavirus (BDV) in human rectal tumor–18 (HRT–18) cell line. In: Proc. $75^{th}$ Conf. Res Workers Anim. Dis., Chicago, IL Nov. 14–15, 1994, 75:P77.

Kapil, S. et al.; 1991. Experimental infection with a virulent pneumoenteric isolate of bovine coronavirus. J. Vet. Diagn. Invest 3:88–89.

Kapil, S. et al.; 1990. Excretion an persistance of the bovine coronavirus in neonatal calves. Arch. Virol. 115:127–132.

Macintyre, G. et al.; 1991a. Hygromycin B therapy of a murine coronaviral hepatitis. Antimicrob. Agents Chemother. 35:2125–2170.

Macintyre G., et al. 1991b. Hygromycine B inhibits synthesis ofmurine coronavirus RNA. Antimicrob. Agents Chemother 35:2630–2633.

Storz, J. et al.; 1981. Enhancement of plaque formation and cell fusion of an enteropathogenic coronavirus by trypsin treatment. Infect. Immun. 31:1214–1222.

Vautherot, J.F. 1981. Plaque assay for titration of bovine enteric coronavirus. J. Gen. Virol. 56:451–455.

Tsunemitsu et al.; 1995. Antigenic and biological comparisons of bovine coronaviruses derived from neonatal alf diarrhea and winter dysentery of adult cattle. Arch. Virol. 140:1303–1311.

*Primary Examiner*—Julie Reeves
*Attorney, Agent, or Firm*—Hovey, Williams, Timmons & Collins

[57] ABSTRACT

New purified and isolated bovine coronavirus (BCV) types (II and III) are described which can be used to create new modified live vaccines for administration to cattle in order to confer immunity against virulent wild-type bovine coronavirus infection. Preferably, a multivalent modified live vaccine is provided for oral-nasal administration which includes the known Type I virus and the new Types II and III virus. Hygromycin B has also demonstrated to be effective for suppressing BCV replication and thus can be administered to cattle as a treatment for the chronic disease and to suppress shedding of BCV in cattle feces.

1 Claim, 1 Drawing Sheet

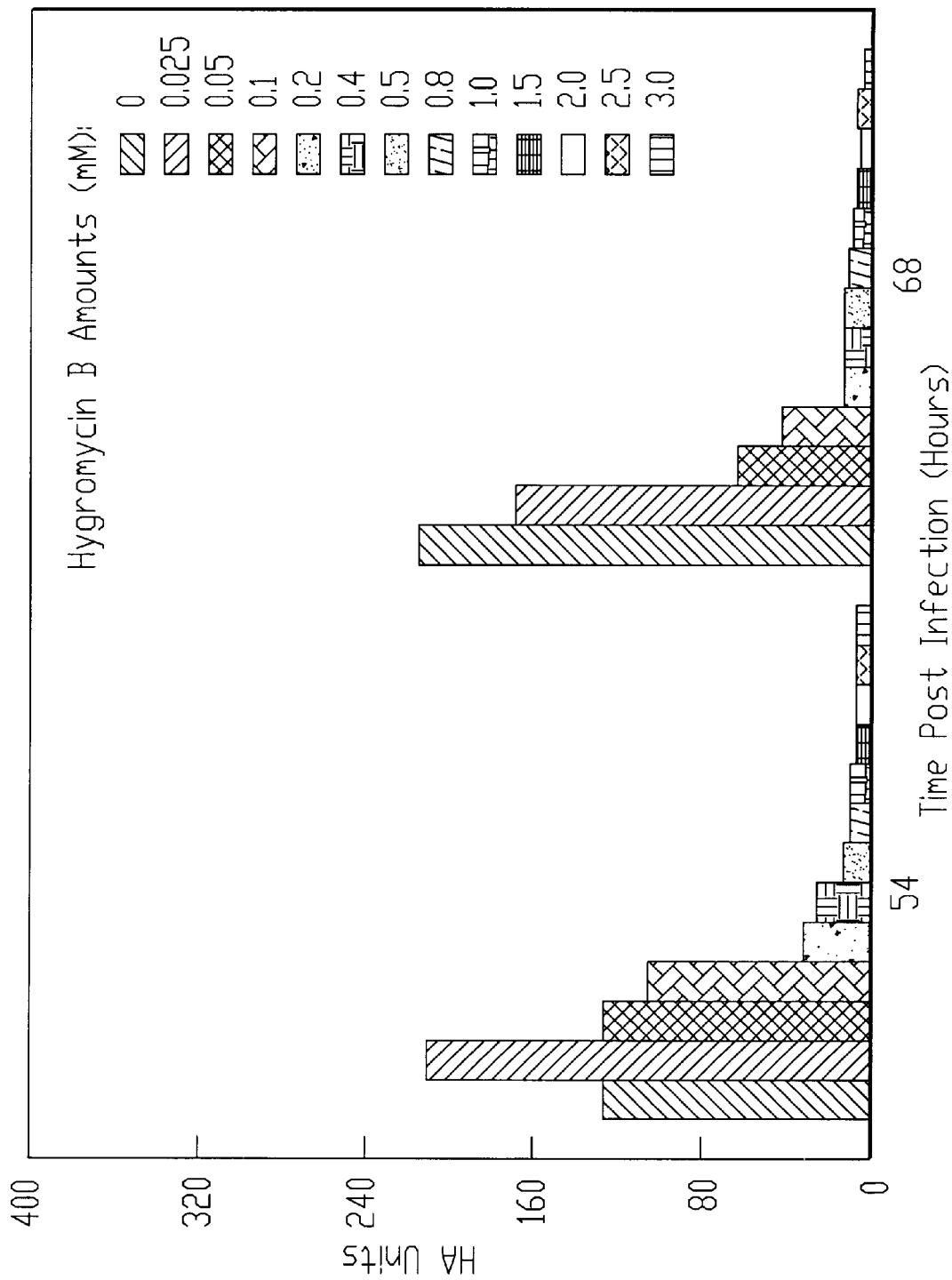

MULTIVALENT BOVINE CORONAVIRUS VACCINE AND METHOD OF TREATING BOVINE CORONAVIRUS INFECTION

This application is a continuation, of application number 08/489,614 filed Jun. 12, 1995, now abandoned.

BACKGROUND OF THE INVENTION

1. Field of the Invention

The present invention is directed to modified live vaccines for administration to cattle (especially newborn calves) in order to immunize the cattle against virulent wild-type bovine coronavirus infections (enteric and respiratory). The vaccines hereof contain low-passaged bovine coronavirus taken from the group consisting of Type II and Type III bovine coronavirus, and mixtures thereof, and may also contain the known Type I bovine coronavirus. The invention also pertains to a method of treating cattle with hygromycin B in sufficient quantities to suppress shedding of bovine coronavirus in the feces of said cattle.

2. Description of the Prior Art

Bovine coronavirus (BCV) is an important cause of enterocolitis and respiratory tract infections in calves and adult cattle. In some instances, the diseases are referred to as calf diarrhea, calf scours or calf enteritis, and winter dysentery in adult cattle. Heretofore, only one serotype of BCV has been described, and modified live virus vaccines have been prepared by extensive passaging of the virulent virus. Such vaccines are described in U.S. Pat. Nos. 3,839,556, 3,838,004 and 3,869,547.

However, in recent years, the known vaccines have proven to be clinically ineffective against many wild-type BCV infections, and indeed such infections are believed to cause a wide range of disease syndromes.

Another problem inherent in bovine coronavirus infections is the lack of effective treatment of cattle post-infection. A primary vector for spread of such infections results from shedding of virulent BCV in the feces of infected animals. To date, there has been no reported treatment for infected cattle which would suppress or eliminate such shedding.

There is accordingly a real and unsatisfied need in the art for new treatment modalities for cattle at risk for BCV infection, both in terms of a more effective anti-BCV vaccine and a treatment to suppress BCV shedding by infected cattle.

SUMMARY OF THE INVENTION

The present invention overcomes the problems outlined above, and provides new modified live BCV cattle vaccines which confer broader immunity against virulent wild-type BCV, as compared with existing vaccines. The invention is predicated upon the discovery of new antigenically distinct isolates of BCV which are referred to as Type II and Type III bovine coronavirus. These Type II and Type III coronavirus are preferably passaged up to about ten times in cell culture which supports the growth of the virus to create modified live vaccines. Excessive cell culture passages of the coronavirus should be avoided. The Type II and Type III BCV can be used individually as monovalent vaccines. More preferably, a multivalent vaccine comprising at least the Type II and Type III BCV is provided and such a vaccine may also contain the conventional Type I BCV (such as that deposited with the ATCC under Accession No. VR-874).

As used herein, Type I, Type II and Type III BCV isolates are defined in terms of the dilution inhibition titers developed in a one-way hemagglutination inhibition (HI) assay. That is, using this assay, Type I BCV has a dilution inhibition titer in the range of 1:512–1:4096; Type II BCV has a dilution inhibition titer of 1:32–1:256; and Type III has a inhibition dilution titer of 1:16 or more. The assay procedure to be used in generating the appropriate dilution inhibition titer data for determining an isolate type is fully described in Example 1.

In preferred forms, each dose of the modified live vaccines of the invention contain about $10^4$ to about $10^8$ plaque forming units (PFU) of bovine coronavirus, most preferably about $10^6$ PFU. In use, the modified live viruses of the invention are administered to calves, typically by oral-nasal inoculation. The most effective treatment is believed to be administration of the vaccine to newborn calves just after birth at least two hours before colostrum feeding.

In another aspect of the invention, it has been found that hygromycin B, a known feed additive for swine and poultry rations, can be administered to cattle as a treatment for chonic BCV infection in calves and adult cattle. Administration of hygromycin B serves to suppress or eliminate shedding of BCV in the feces of cattle, thus minimizing a primary source of infection. Typically, hygromycin B is simply fed with the calf or cattle ration in amounts to at least suppress shedding of BCV in the feces. A suitable dosage of hygromycin B would be from about 6–9 g of the drug per ton of cattle feed.

BRIEF DESCRIPTION OF THE DRAWING

FIG. 1 is a graphical representation setting forth the effect of hygromycin B upon cell culture viral replication of bovine coronavirus, as described in Example 4.

DETAILED DESCRIPTION OF THE PREFERRED EMBODIMENTS

The following examples describe the isolation and characterization of new BCV isolates in accordance with the invention, and moreover describes a manner of use thereof. It is be understood that these examples are set forth by way of illustration only, and nothing therein shall be taken as a limitation upon the overall scope of the invention.

EXAMPLE 1

Hemagglutination Assay (HA)/One-Way Hemagglutination Inhibition (HI) Assay Using 25 Fecal Suspensions Positive for Bovine Coronavirus Wisconsin Samples A total of 20 bovine fecal samples were obtained from The Wisconsin Animal Health Laboratory, Madison, Wis. Each of these samples had previously been determined by direct electron microscopy to contain bovine coronavirus, but were free of other known bovine virus. Each sample was diluted 1:10 v/v with calcium and magnesium ion-free PBS (CMF-PBS at pH 7.2).

Each sample was then centrifuged at 3000 rpm for 10 minutes and the clear supernatant was pipetted and saved. Each supernatant was then passed through a 0.45 micron, low protein-absorbing syringe filter. The filtrate of each sample was then subsequently assayed.

The first assay step was to determine the number of HAU (hemagglutination units) in each sample. Specifically, the BCV titer in each sample was determined using mouse erythrocytes suspended 0.5% v/v in PBS, pH 7.2, and containing 0.1% by weight BSA fraction V. First, successive two-fold dilutions (from 2-4096 fold) of each filtrate coronavirus sample were made using the PBS/BSA solution. Twenty-five microliters of each dilution were then placed in individual wells of a 96-well V-bottom microtiter plate, followed by the addition of an additional 25 microliters of the PBS/BSA solution into each well. Next, 25 microliters of the mouse erythrocyte suspension was added to each well. Thereupon, the side walls of the plate were tapped 4–5 times to insure mixing of the liquid fractions in each well. The plate was then covered and kept at 10° C. for 90 minutes. The plate was then placed on a mirrored viewer. Each well was then visually examined to determine the hemagglutination end point titer for each sample of filtrate.

This titer data was used to determine the extent of dilution required to achieve, for each sample, a level of about 4–8 HAU/25 μl of filtrate sample. These dilutions were carried out in individual Eppendorf tubes, using the PBS/BSA solution.

Each standardized sample was then subjected to a hemagglutination inhibition (HI) assay. This assay is basically described by Sato et al., "Hemagglutination by Calf Diarrhea Coronavirus", *Vet. Microbiology,* 2 (1977) 83–87, incorporated by reference herein. The assay used in the present invention as a way to determine whether a given BCV is Type I, Type II or Type III virus is very similar to that described by Sato et al. In particular, HI assay used in connection with the present invention makes use of an anti-BCV serum such as the standard hyperimmune anti-BCV serum obtained from National Veterinary Services Laboratory, Ames, Iowa. A common serum obtained from this source is Lot No. 320BDV8801. The serum was first diluted (0.2 ml serum in 0.5 ml PBS) and heat inactivated by heating to 56° C. and maintaining this temperature for 30 minutes. Next, the inactivated serum was treated by the addition of kaolin (0.4 ml of 25% kaolin), followed by centrifugation (15,000 g for 1 min.). The supernatant was then mixed with 0.2 ml of packed mouse erythrocyte per ml of supernatant. The treated serum was then maintained at 37° C. for 1 hour. Thereafter, the treated serum was centrifuged (15,000 g for 1 min.) and the supernatant was used in the HI assay.

Increasing two-fold dilutions of the treated serum supernatant were then prepared and 25 μl of each dilution were placed in individual wells of a 96-well V-bottom microtiter plate. Twenty-five μl of each of the standardized filtrate samples were then added to each well followed by tapping and mixing. The plate was then incubated at 37° C. for 1 hour. At this point, 25 μl of the previously described mouse erythrocyte suspension was added to each well, followed by tapping and mixing. A second incubation at 10° C. was carried out for 90 minutes.

At the completion of the second incubation, the plate was visually examined to determine the extent of inhibition of hemagglutinating activity of each virus by the serum antibodies. Full inhibition is evidenced by the formation of a small "button" in the center of the wells. Lack of inhibition is shown by matting at the bottom of the wells.

Of the 20 starting samples, only four were fully inhibited by the treated serum, and it was concluded that these samples contained the known Type I BCV virus (WI-1.SK). Eight starting samples were not inhibited, two were inhibited up to 1:2 dilution, and two were inhibited up to 1:4 dilution, two were inhibited up to 1:8 dilution and one was inhibited up to 1:16 dilution. These 15 samples were therefore BCV Type III virus. A single sample was inhibited up to 1:128 dilution, and this sample was deemed to include BCV Type II virus.

This experiment demonstrated that only a small number of the starting samples contained the Type I strain, whereas 15 of the samples contained the Type III strain. Accordingly, the known vaccines against the Type I strain would not confer immunogenicity against the Type III strains. It is postulated that the Types II and III BCV virus evolved from the originally isolated Type I virus under immunological pressure or may have evolved independently of the Type I virus.

California Samples

Six California samples were tested in exactly the same manner as the Wisconsin samples. All six of the California samples were BCV Type III.

EXAMPLE 2

Genetic Purification of BCV Virus Strains and Formation of Seed Stocks

Each of the 26 supernatants containing BCV as described in Example 1 were inoculated into cell culture.

Specifically, each cell culture contained human rectal tumor (HRT-18) cells obtained from Dr. David Benfield, University of South Dakota, Brookings, S. Dak. The HRT-189 cell line was deposited with the ATCC, 10801 University Blvd., Manassas, Va. 20110-2209, on Sep. 18, 1998, under accession number CRL-12567. These cells were screened and free of Mycoplasma sp., bovine viral diarrhea virus (BVD) and any contaminating bacteria. These cells were plated in 25 $cm^2$ flasks and incubated at 37° C. until the monolayer became confluent (usually 2–3 days). Each monolayer was then quickly washed with CMF-PBS containing 5 μg/ml of trypsin. 0.2 ml of each filtered and diluted supernatant of the 26 samples was then added to a respective treated cell culture. These flasks were rocked every 15 minutes during incubation at 37° C. for 1 hour (original passage). Thereafter, 4–5 ml of MEM (minimal essential medium) was added to each flask. The MEM contained 5 μg/ml of both trypsin and pancreatin. Each flask was then further incubated at 37° C. for a period of about 4–5 days with daily observation to determine cytopathic effect (CPE). CPE was determined by either rounding detachment or syncytium formation.

All of the 26 flasks were then tested in three different manners to determine and confirm the presence of BCV. First, each cell culture was tested by direct fluorescent antibody assay using FITC-labeled anti-BCV conjugate supplied by National Veterinary Services Laboratory, Ames, Iowa. The label directions with the conjugate were followed in performing the assay. Second, the amount of virus in each cell culture was determined using the HA assay described in Example 1. Third, each cell culture was checked for contaminating bovine viruses, using direct fluorescent antibody techniques, i.e., each culture was free of bovine rotavirus, IBR, BVD, bovine adenovirus, and bovine reovirus. Of the 26 cell cultures, 14 were confirmed to have propagated BCV; 8 of these cultures were from the Wisconsin samples; and 6 were from California.

The BCV-positive samples were harvested from each cell culture by three freeze-thaw cycles followed by centrifugation to pellet the cells. The cell-free supernatant is aliquoted (1 ml) and stored at −70° C.

In the next step, the 14 BCV isolates were plaque purified using the technique described in Kapil et al., "Plaque Variations in Clinical Isolates of Bovine Coronavirus," J. Vet. Diagn. Invest. 7 (1995) 538–539. Briefly, HRT-18 cells were plated in 6-well culture dishes and grown in MEM supplemented with 10% fetal calf serum (FCS), L-glutamine, penicillin and streptomycin. After 3–4 days propagation at 37° C., the resulting confluent monolayers were washed with CMF-PBS.

The 14 frozen harvested BCV samples were thawed just prior to use and diluted ten-fold in CMF-PBS. One hundred $\mu$l of each dilution ($10^{-1}$ to $10^{-6}$) were then placed in each well of the tissue culture dish. The culture dishes were incubated at 37° C. for 1 hour, with rocking every 15 minutes. After incubation, each well was quickly washed with 1 ml of CMF-PBS. Next, 4 ml of MEM supplemented with 1% w/v agarose at 45° C. was added to each well. The agarose was then allowed to solidify in each well, which usually took about 30 minutes at room temperature. The tissue culture plates were then inverted and incubated for up to three days at 37° C. The viral plaques appeared after about two days incubation. At the end of the incubation period, each viral plaque was singly harvested by pipette, about 50 $\mu$l of CMF-PBS was added, and the plaques were frozen at −70° C. There were about 69 resulting genetically pure plaques.

One plaque per viral isolate was selected for serial passage and propagation to form about 2 liters of virus. In particular, the selected plaques were thawed, diluted with 5–10 ml of the CMF-PBS, and about one-half ml of each dilution was added to individual 150 cm$^2$ tissue culture flasks. Incubation at 37° C. over a period of 3 days followed. Four additional passages were carried out in the same fashion, resulting in a total of 6 passages, namely the original passage, plaque purification, and the four subsequent passages. At the end of the passage sequence, there was approximately 25 ml of passage 6 for each of the 14 isolates. In order to generate large volumes of each isolate, ½ ml of each isolate was placed in a respective 150 cm$^2$ flask. Incubation at 37° C. followed as passage 7, and the collected quantities from each flask for each isolate were pooled. Each pooled isolate constituted a modified live vaccine.

A total of 11 monovalent modified live vaccines were successfully produced: two are Type I vaccines, one is a Type II vaccine, and eight are Type III vaccines.

EXAMPLE 3

Use of Multivalent Modified Live Vaccines

The Type I, Type II and Type III isolates of Example 2 are administered in vivo by oral-nasal inoculation of approximately ½ ml of each isolate (each such dose containing about $10^6$ PFU of BCV). Such inoculation is given to colostrum-deprived calves immediately after birth. These calves are allowed colostrum two hours after birth. The inoculations confer immunity upon the calves at least against homologous types of BCV.

A multivalent vaccine is prepared by mixing equal quantities of selected Type I, Type II and Type III BCV isolates described in Example II. In like manner, a multivalent vaccine can be prepared using only Type II and Type III BCV isolates, if desired. The use of such multivalent vaccines is exactly as described above.

EXAMPLE 4

Viral Suppression Using Hygromycin B

In this example, the effect of a feed additive drug, hygromycin B, on BCV in cell culture was tested. In particular, three replicates each of individual cell cultures containing a Wisconsin isolate (WI-1.SK, a Type I BCV) were inoculated with varying amounts of hygromycin B and viral growth over time was monitored.

Each of the cell cultures contained HRT-18 cells treated as described in Example 2. Confluent monolayers in each culture were then inoculated with a dose containing about 32 HAU of the WI-1.SK isolate along with selected amounts of hygromycin B, ranging from zero (control) to 3 mM hygromycin B. Each of the cell cultures was then incubated at 37° C. for varying periods up to 90 hours. In order to determine the amount of virus in HAU over time, respective cell cultures were subjected to three freeze-thaw cycles and the HA analysis described previously was conducted on the supernatants.

The attached Figure illustrates the results of this test after 54 and 68 hours incubation following viral inoculation. As can be seen, those cultures inoculated with at least 0.4 mM hygromycin B exhibited very low, negligible viral growth; indeed, the results may simply be the effect of the original virus.

These results demonstrate that hygromycin B inhibits BCV replication in vitro, inasmuch as the drug was effective against all isolates of BCV tested irrespective of their antigenic composition and differences. This is strongly indicative that the drug will also suppress BCV replication in vivo.

I claim:

1. An isolated bovine coronavirus, wherein the hemagglutinating activity of the bovine coronavirus (BCV) is fully inhibited at an antibody titer in the range of from about 1:1 to 1:16 and is uninhibited at a titer of about 1:32 and above, in the one-way mouse erythrocyte hemagglutination inhibition assay of Example 1 using standard National Veterinary Services Laboratory hyperimmune anti-BCV serum.

* * * * *